United States Patent
Raycheck et al.

(10) Patent No.: US 11,654,061 B2
(45) Date of Patent: May 23, 2023

(54) ABSORBENT ARTICLES WITH COMPONENTS FOR A UNIFORM APPEARANCE

(71) Applicant: The Procter & Gamble Company, Cincinnati, OH (US)

(72) Inventors: Jeromy T. Raycheck, South Lebanon, OH (US); Tanner L. Williams, Loveland, OH (US); Christine A. Methena, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 925 days.

(21) Appl. No.: 16/541,216

(22) Filed: Aug. 15, 2019

(65) Prior Publication Data

US 2020/0060888 A1    Feb. 27, 2020

Related U.S. Application Data

(60) Provisional application No. 62/726,575, filed on Sep. 4, 2018, provisional application No. 62/720,170, filed on Aug. 21, 2018.

(51) Int. Cl.
*A61F 13/49* (2006.01)
*A61F 13/56* (2006.01)
*A61F 13/514* (2006.01)

(52) U.S. Cl.
CPC .... *A61F 13/4902* (2013.01); *A61F 13/49014* (2013.01); *A61F 13/565* (2013.01); *A61F 13/5148* (2013.01); *A61F 2013/51409* (2013.01)

(58) Field of Classification Search
CPC ........... A61F 13/4902; A61F 13/49014; A61F 13/565; A61F 13/5148; A61F 13/51474; A61F 2013/51409
See application file for complete search history.

(56) References Cited

U.S. PATENT DOCUMENTS 3,848,594 A    11/1974 Buell
3,860,003 A    1/1975 Buell
(Continued)

FOREIGN PATENT DOCUMENTS

WO    WO 95/16746    6/1995
WO    WO 2004/017885    3/2004
WO    WO 2016/069269    5/2016

OTHER PUBLICATIONS

International Search Report and Written Opinion; Application Ser. No. PCT/US2019/046476; dated Jan. 15, 2020, 12 pages.

*Primary Examiner* — Susan S Su
(74) *Attorney, Agent, or Firm* — Amanda Herman Berghauer; Christian M. Best

(57) ABSTRACT

A taped absorbent article is provided. The taped absorbent article includes a chassis comprising a topsheet, a backsheet, an absorbent core positioned at least partially intermediate the topsheet and the backsheet, and an outer cover nonwoven material joined to the backsheet. The outer cover nonwoven material comprises a first mechanical bond pattern. The taped absorbent article includes a discrete ear laminate joined to the chassis. The discrete ear laminate includes a first nonwoven material having a garment-facing surface, a second nonwoven material having a wearer-facing surface, a plurality of ultrasonic bonds, and an elastic member positioned at least partially intermediate the first and second nonwoven materials. The garment-facing surface of the first nonwoven material comprises a second mechanical bond pattern. The first and second mechanical bond patterns are substantially the same. The outer cover nonwoven material is substantially the same as, or the same as, the first nonwoven material.

10 Claims, 15 Drawing Sheets

(56) References Cited

U.S. PATENT DOCUMENTS

| | | |
|---|---|---|
| 4,610,678 A | 9/1986 | Weisman et al. |
| 4,662,875 A | 5/1987 | Hirotsu et al. |
| 4,673,402 A | 6/1987 | Weisman et al. |
| 4,834,735 A | 5/1989 | Alemany et al. |
| 4,846,815 A | 7/1989 | Molloy |
| 4,888,231 A | 12/1989 | Angstadt |
| 4,892,536 A | 1/1990 | DesMarais et al. |
| 4,894,060 A | 1/1990 | Nestegard |
| 4,946,527 A | 8/1990 | Battrell |
| 4,990,147 A | 2/1991 | Freeland |
| 5,037,416 A | 8/1991 | Allen et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,260,345 A | 11/1993 | DesMarais et al. |
| 5,269,775 A | 12/1993 | Freeland et al. |
| 5,342,338 A | 8/1994 | Roe |
| 5,387,207 A | 2/1995 | Dyer et al. |
| 5,397,316 A | 3/1995 | Lavon et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,865,823 A | 2/1999 | Curro |
| 5,993,432 A | 11/1999 | Lodge et al. |
| 6,004,306 A | 12/1999 | Robles et al. |
| 6,107,537 A | 8/2000 | Elder et al. |
| 6,120,487 A | 9/2000 | Ashton |
| 6,410,129 B2 | 6/2002 | Zhang et al. |
| 6,432,098 B1 | 8/2002 | Kline et al. |
| 6,572,595 B1 | 6/2003 | Klemp et al. |
| 6,677,258 B2 | 1/2004 | Carroll et al. |
| 6,878,433 B2 | 4/2005 | Curro et al. |
| 7,435,243 B2 | 10/2008 | Miyamoto |
| 7,806,883 B2 | 10/2010 | Fossum et al. |
| 7,819,853 B2 | 10/2010 | Desai et al. |
| 8,062,279 B2 | 11/2011 | Miyamoto |
| 8,454,571 B2 | 6/2013 | Rezai et al. |
| 8,618,350 B2 | 12/2013 | Mansfield |
| 8,795,809 B2 | 8/2014 | Mansfield |
| 8,939,957 B2 | 1/2015 | Ray et al. |
| 9,301,889 B2 | 4/2016 | Miyamoto |
| 9,358,161 B2 | 6/2016 | Lawson et al. |
| 2006/0149209 A1 | 7/2006 | Mal et al. |
| 2007/0167929 A1* | 7/2007 | Fossum .................. B32B 5/022 604/385.31 |
| 2009/0258210 A1 | 10/2009 | Muslet et al. |
| 2010/0298796 A1 | 11/2010 | Horn et al. |
| 2012/0157953 A1* | 6/2012 | Ashton .................. A61F 13/496 604/385.16 |
| 2012/0238980 A1 | 9/2012 | Lam et al. |
| 2012/0316526 A1 | 12/2012 | Rosati et al. |
| 2012/0316532 A1 | 12/2012 | Mccormick |
| 2013/0082418 A1 | 4/2013 | Curro et al. |
| 2013/0306226 A1 | 11/2013 | Zink |
| 2015/0126955 A1 | 5/2015 | Sauer et al. |
| 2016/0270972 A1 | 9/2016 | Surushe et al. |
| 2017/0027775 A1 | 2/2017 | Barnes et al. |
| 2017/0056256 A1 | 3/2017 | Smith et al. |
| 2018/0042777 A1 | 2/2018 | Dalal |
| 2018/0229216 A1 | 8/2018 | Smith et al. |

* cited by examiner

ABSORBENT ARTICLES WITH COMPONENTS FOR A UNIFORM APPEARANCE

CROSS REFERENCE TO RELATED APPLICATION

This application claims the benefit, under 35 U.S.C. § 119(e), to U.S. Provisional Patent Application No. 62/726,575, filed on Sep. 4, 2018, and U.S. Provisional Patent Application No. 62/720,170, filed on Aug. 21, 2018, which are both herein incorporated by reference in their entirety.

FIELD

The present disclosure is generally directed to absorbent articles with components for a uniform appearance.

BACKGROUND

Absorbent articles are used to contain and absorb bodily exudates (i.e., urine, bowel movements, and menses) in infants, children, and adults. Taped absorbent articles, such as diapers and adult incontinence products, may comprise discrete ear laminates. These discrete ear laminates may comprise a first nonwoven material, a second nonwoven material, and an elastic member positioned at least partially between the first and second nonwoven materials. The discrete ear laminates are used to connect a front waist region and a back waist region of the taped absorbent article upon donning and, as such, typically include a fastener. The discrete ear laminates may be attached to the front waist region and may releasably join to the back waist region or may be attached to the back waist region and may releasably join to the front waist region. These taped absorbent articles may have outer cover nonwoven materials or other nonwoven materials, such as nonwoven topsheets. Typically, the nonwoven materials in absorbent articles for different components are different nonwoven materials, leading to increased cost from sourcing, qualifying, and complexity in the supply chain. This further leads to absorbent articles that appear modular in different components compared to a uniform, garment-like appearance. As such, nonwoven materials used in absorbent articles should be improved.

SUMMARY

The present disclosure provides absorbent articles that comprise at least 2 components with substantially the same, or the same, nonwoven materials. Having at least 2 components with substantially the same, or the same, nonwoven materials achieves a more uniform, garment-like appearance of absorbent articles and the perception of high quality to consumers. Additionally, having at least 2 components with substantially the same, or the same, nonwoven materials achieves supply chain and qualification simplicity and reduces costs in that a higher volume of one particular nonwoven material is being purchased for incorporation into absorbent articles. Example absorbent article components that may comprise substantially the same, or the same, nonwoven material may be at least two of: a first nonwoven material of a discrete ear laminate, a second nonwoven material of a discrete ear laminate, an outer cover nonwoven material, a topsheet, a nonwoven material of a belt, a nonwoven material of a cuff, a landing zone, and a nonwoven material of a waistband, for example. In some instances, all or more than 2 of the nonwoven materials in an absorbent article may be the substantially the same, or the same.

At least 2 nonwoven materials in an absorbent article (whether the same, substantially the same, or different) may comprise a pattern of indicia (e.g., printing), a pattern of three-dimensional features, a pattern of apertures, and/or mechanical bond patterns that may be substantially the same, or the same. This matching of a pattern of indicia, a pattern of apertures, a pattern of three-dimensional features, apertures, and/or mechanical bond patterns leads to uniformity between the various nonwoven components and thereby the consumer perception of high quality absorbent articles. Even if the at least two nonwoven materials are not the same, or substantially the same, having a pattern of indicia, a pattern of three-dimensional features, a pattern of apertures, and/or mechanical bond patterns being the substantially the same, or the same, may lead to a more uniform, garment-like absorbent article.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the absorbent articles with components for a uniform appearance disclosed herein. One or more examples of these non-limiting forms are illustrated in the accompanying drawings. Those of ordinary skill in the art will understand that the absorbent articles with components for a uniform appearance described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Mechanical bonds" means bonds formed in a material by embossing or calendaring, thermal energy, and/or pressure welding, and not by ultrasonic bonding.

"Ultrasonic bonds" means bonds formed in a material using an ultrasonic horn and an anvil with protruding nubs, using high frequency sound.

"Substantially the same" for nonwoven materials means a material designed with the intent of being the same, but having some variation in, for example, basis weight, pore size, that is typical for process tolerances in nonwoven materials.

"Substantially the same" for mechanical bonds means the mechanical bonds are design to be the same, but through some process tolerances are not exactly the same. Substantially the same also means the same mechanical bonds but with ultrasonic bonds formed over at least some of them. Stated another way, the mechanical bond should be compared independent of the ultrasonic bonds.

General Description of an Absorbent Article

Figure 1:
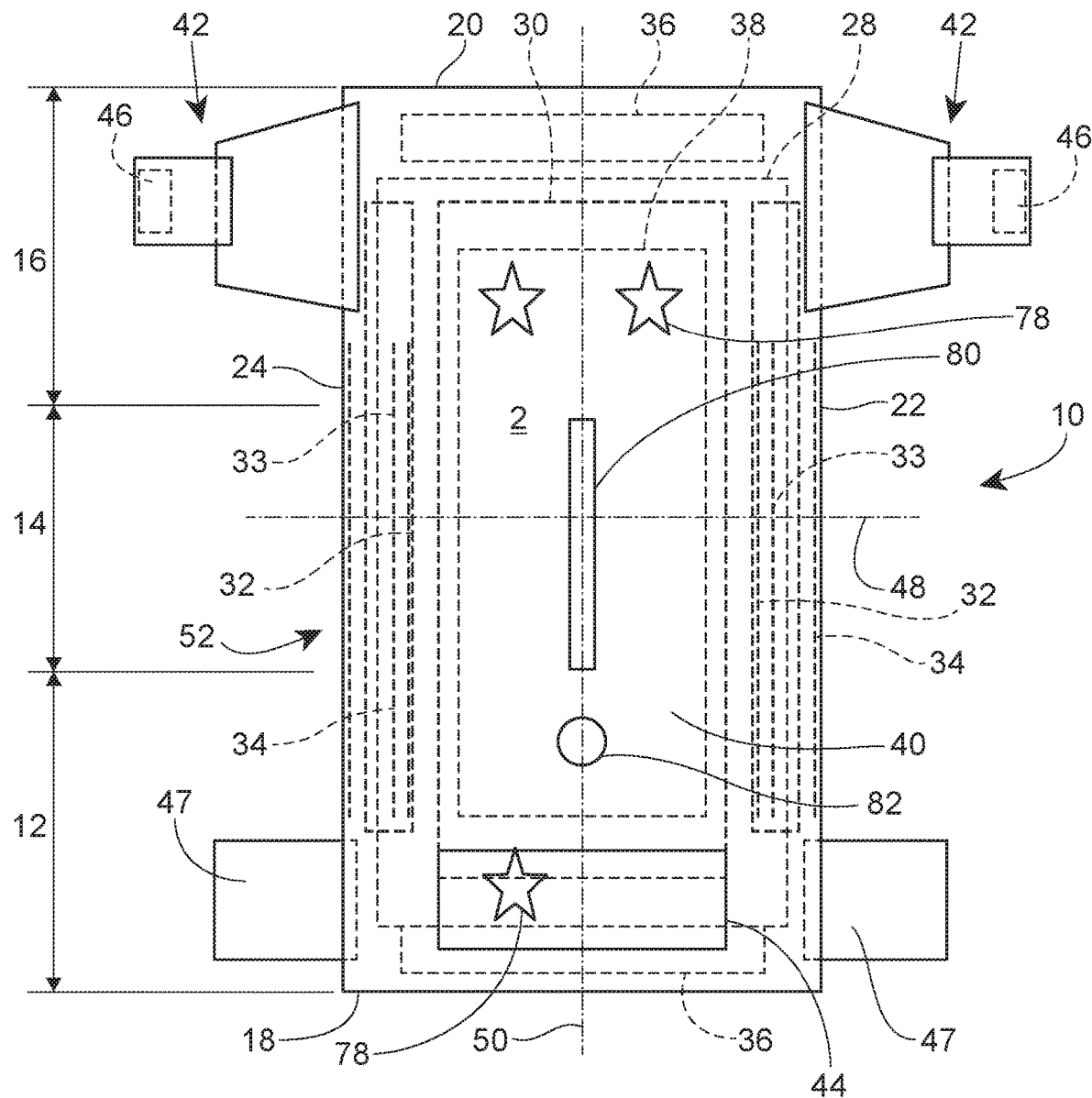
FIG. 1 is a plan view of an example absorbent article in the form of a taped diaper, garment-facing surface facing the viewer, in a flat laid-out state.
Figure 2:
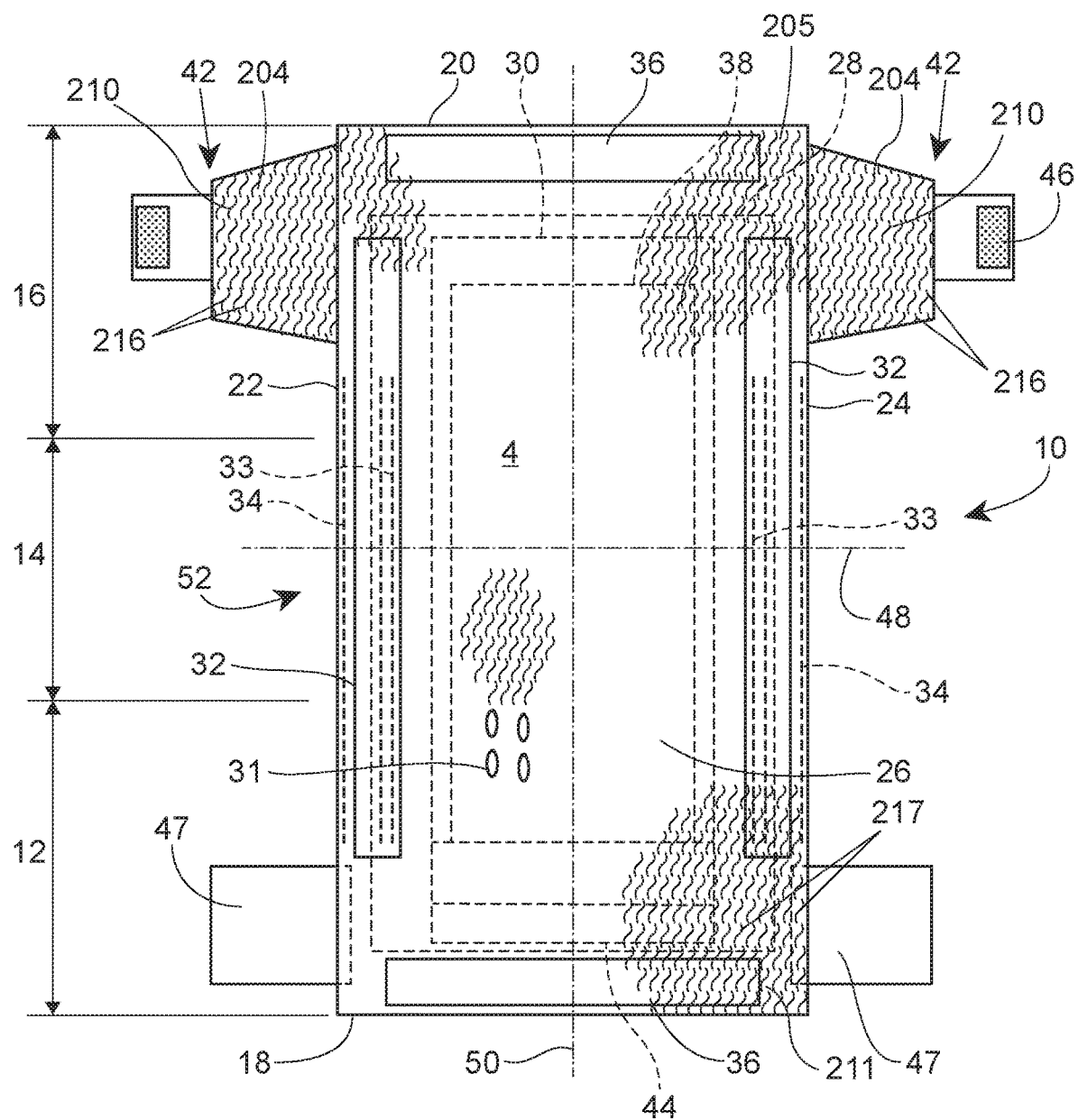
FIG. 2 is a plan view of the example absorbent article of FIG. 1, wearer-facing surface facing the viewer, in a flat laid-out state.
Figure 3:
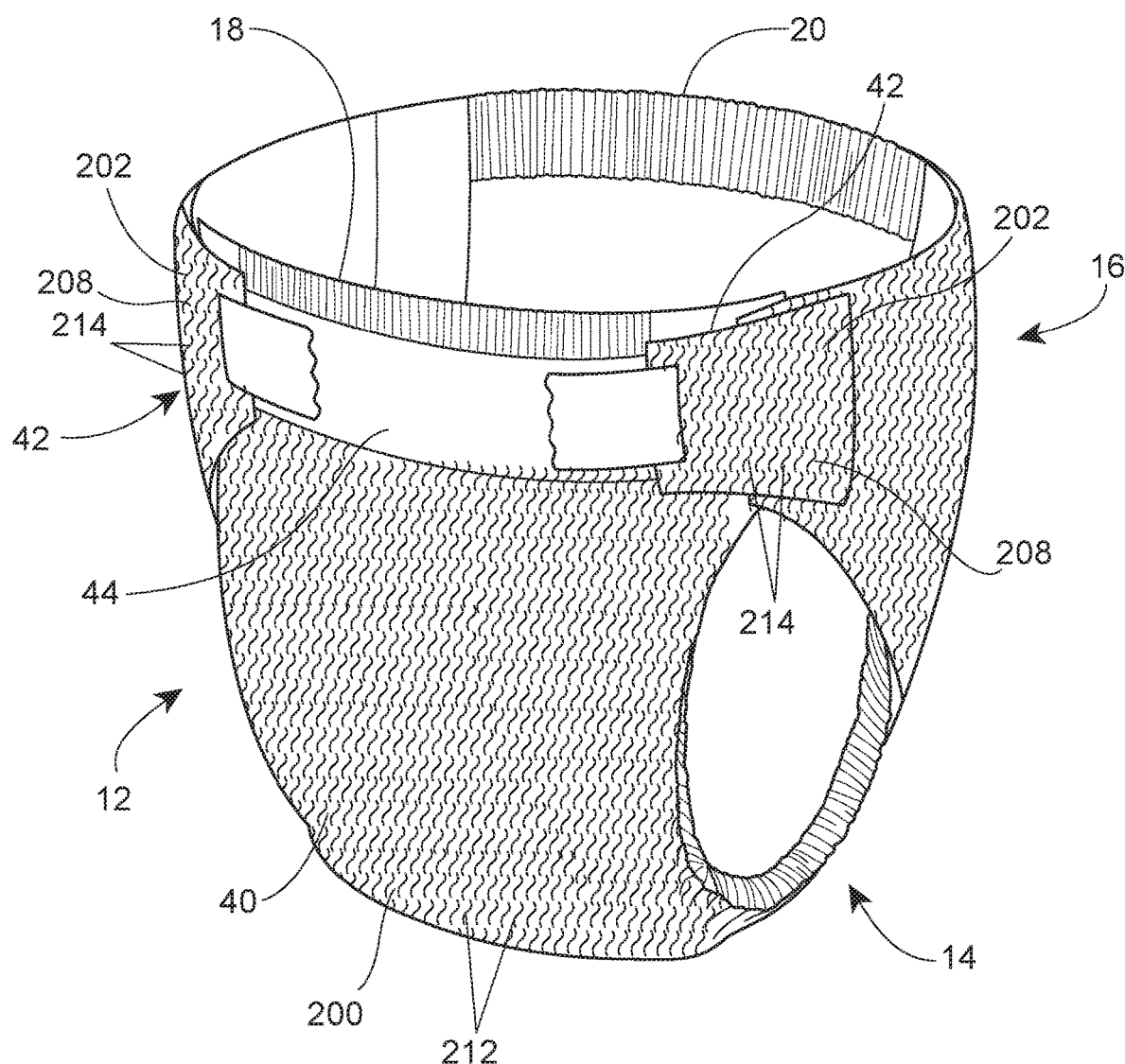
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 (e.g., a discrete ear laminate) in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
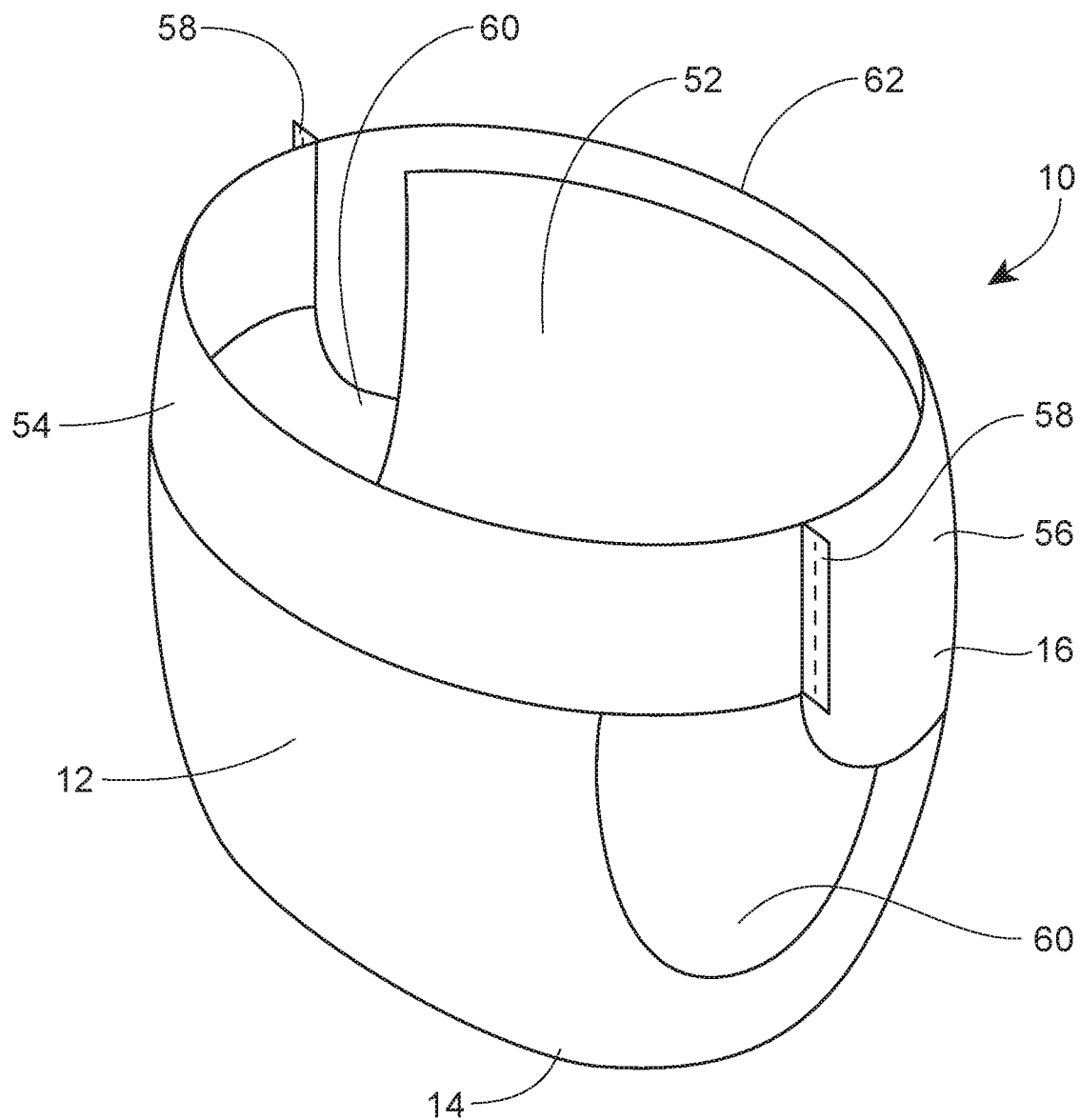
FIG. 4 is a front perspective view of an absorbent article in the form of a pant.
Figure 5:
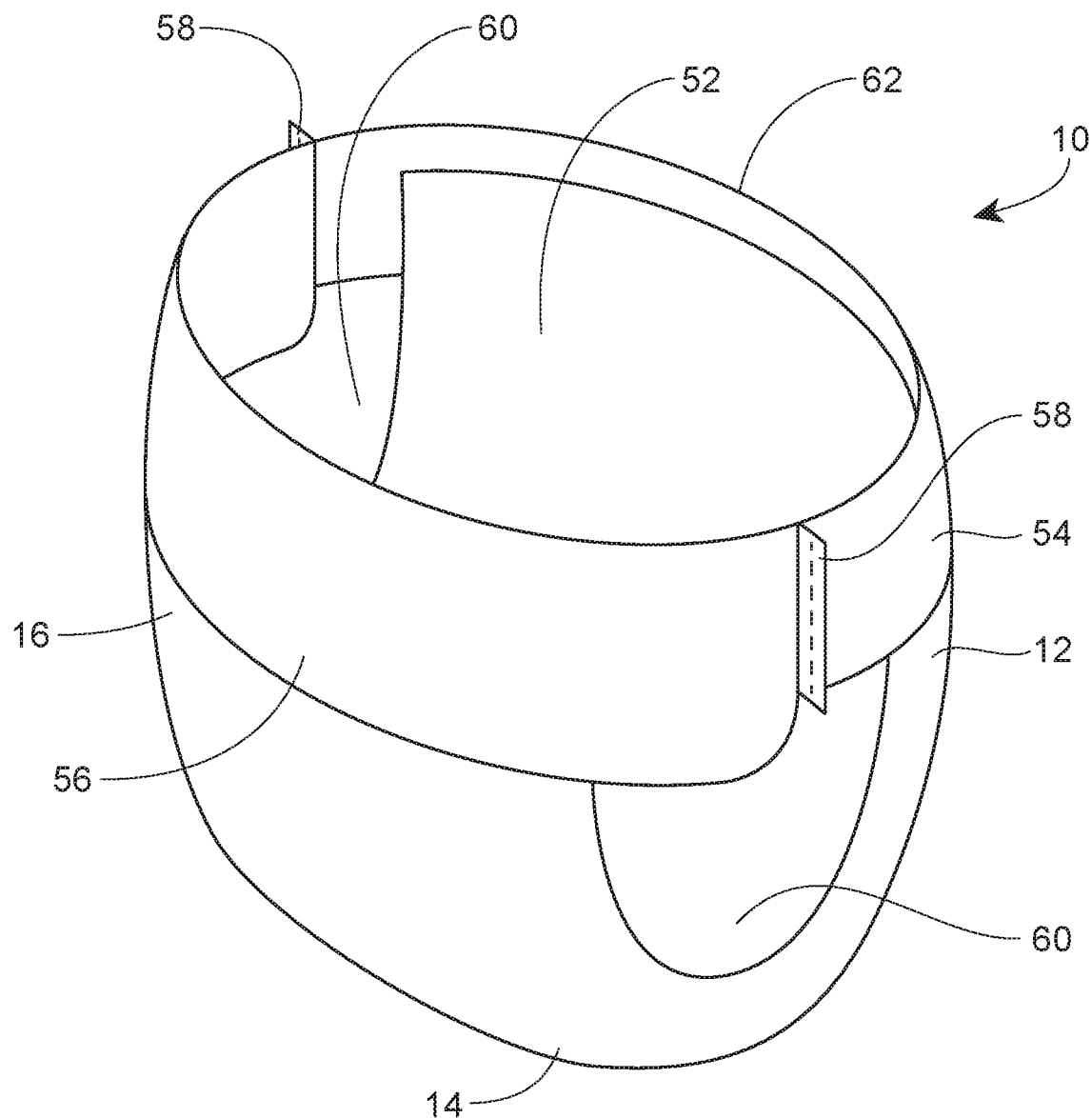
FIG. 5 is a rear perspective view of the absorbent article of FIG. 4.
Figure 6:
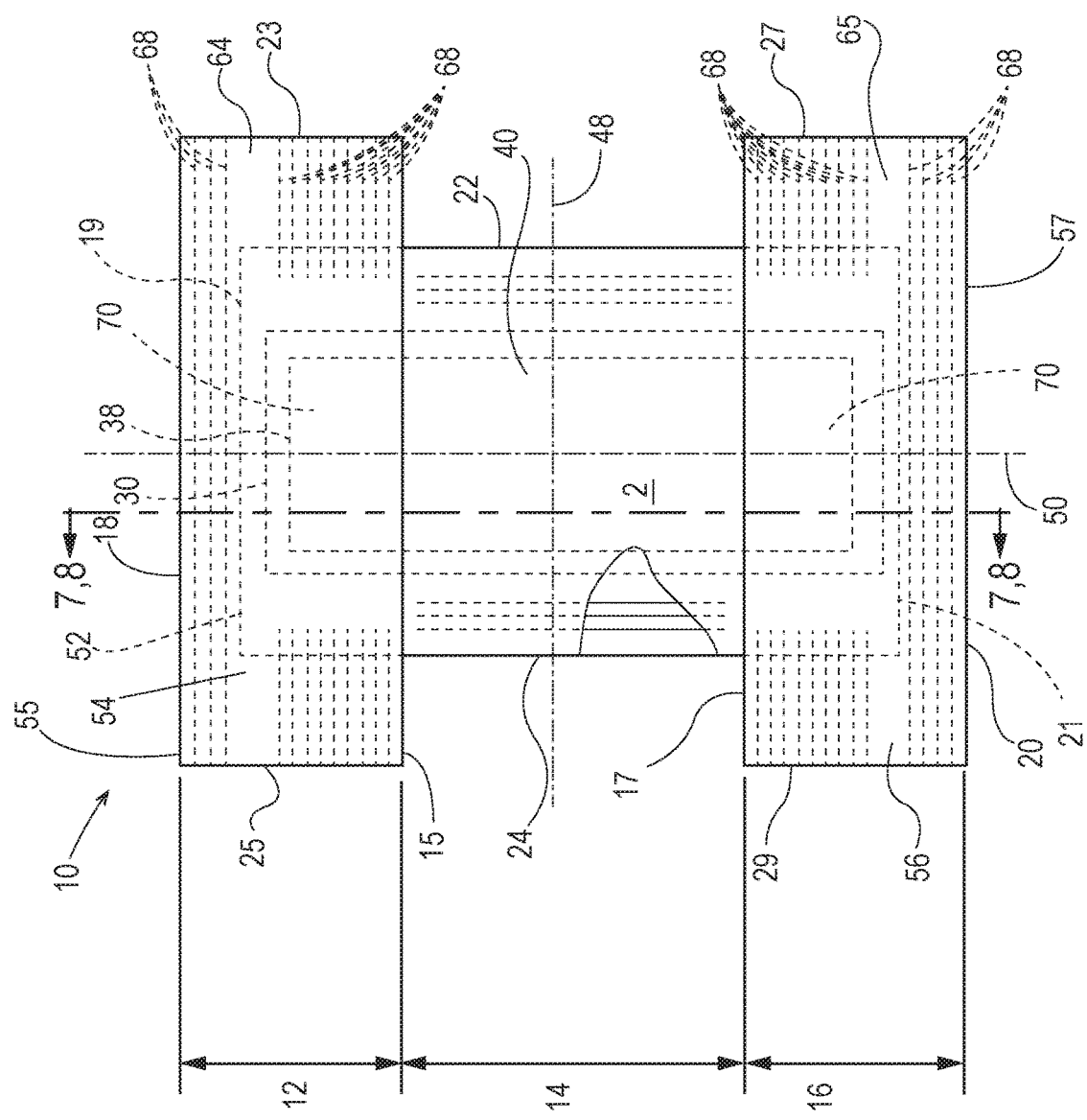
FIG. 6 is a plan view of the absorbent article of FIG. 4, laid flat, with a garment-facing surface facing the viewer.
Figure 7:
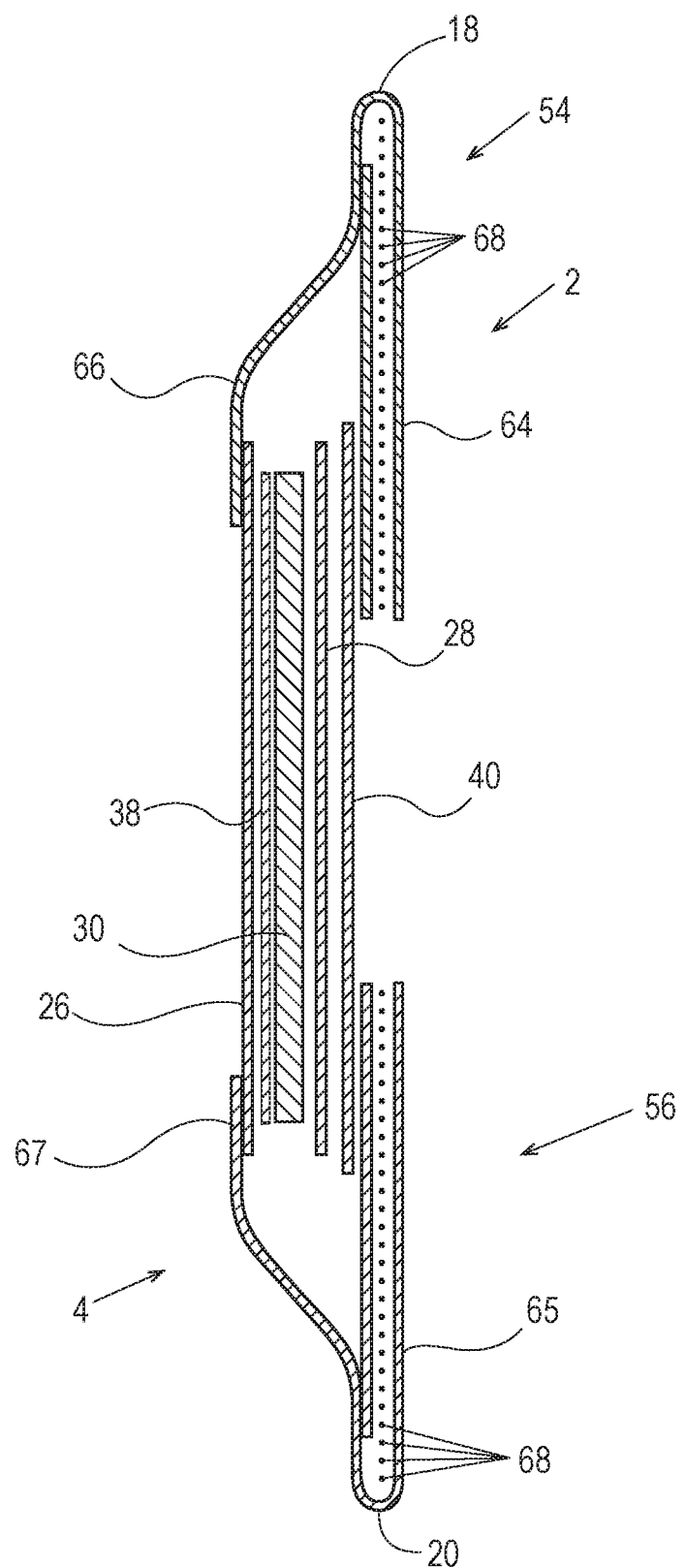
FIG. 7 is a cross-sectional view of the absorbent article taken about line 7-7 of FIG. 6.
Figure 8:
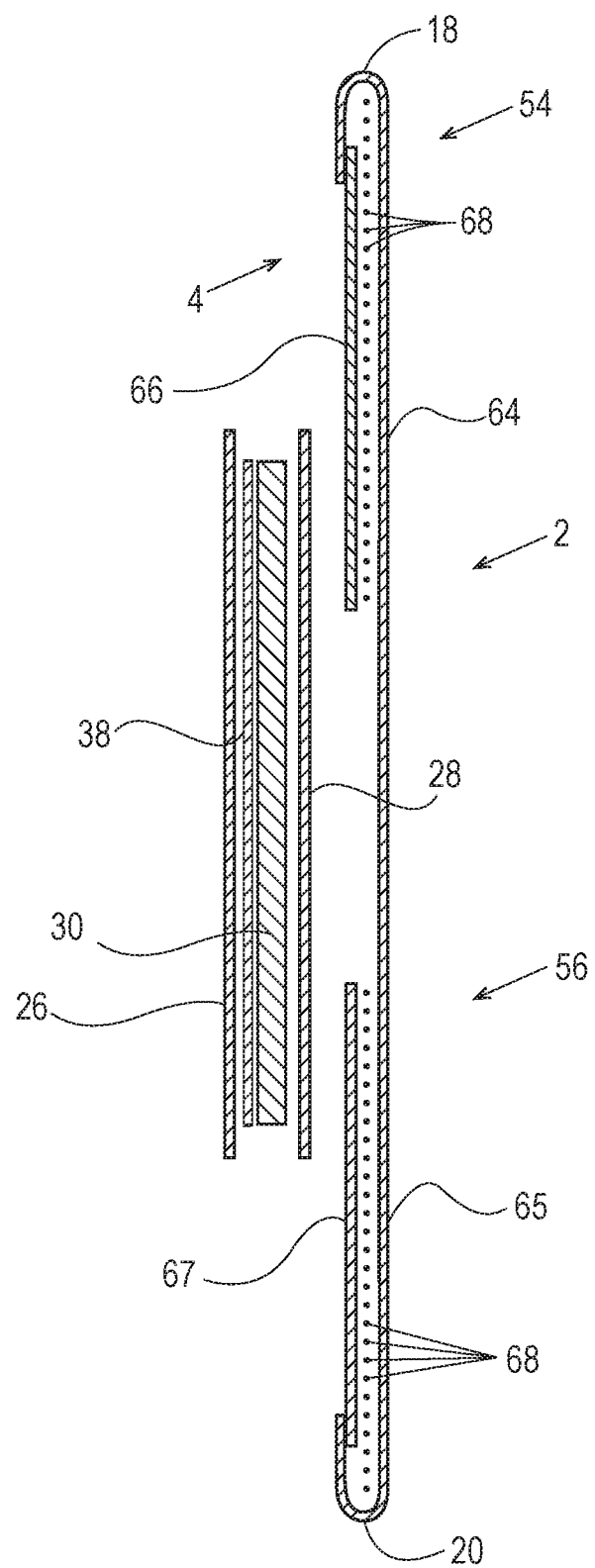
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous. Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Nonwoven materials of the belts 54, 56 may comprise mechanical bonds patterns, patterns of apertures, patterns of indicia, and/or patterns of three-dimensional features.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 2, element 31), may have any suitable three-dimensional features, and/or may have a plurality of embossments (e.g., a mechanical bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheet 26 may comprise mechanical bonds patterns, patterns of apertures, patterns of indicia, and/or patterns of three-dimensional features.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise mechanical bonds patterns, patterns of apertures, patterns of indicia, and/or patterns of three-dimensional features.

Absorbent Core

Figure 9:
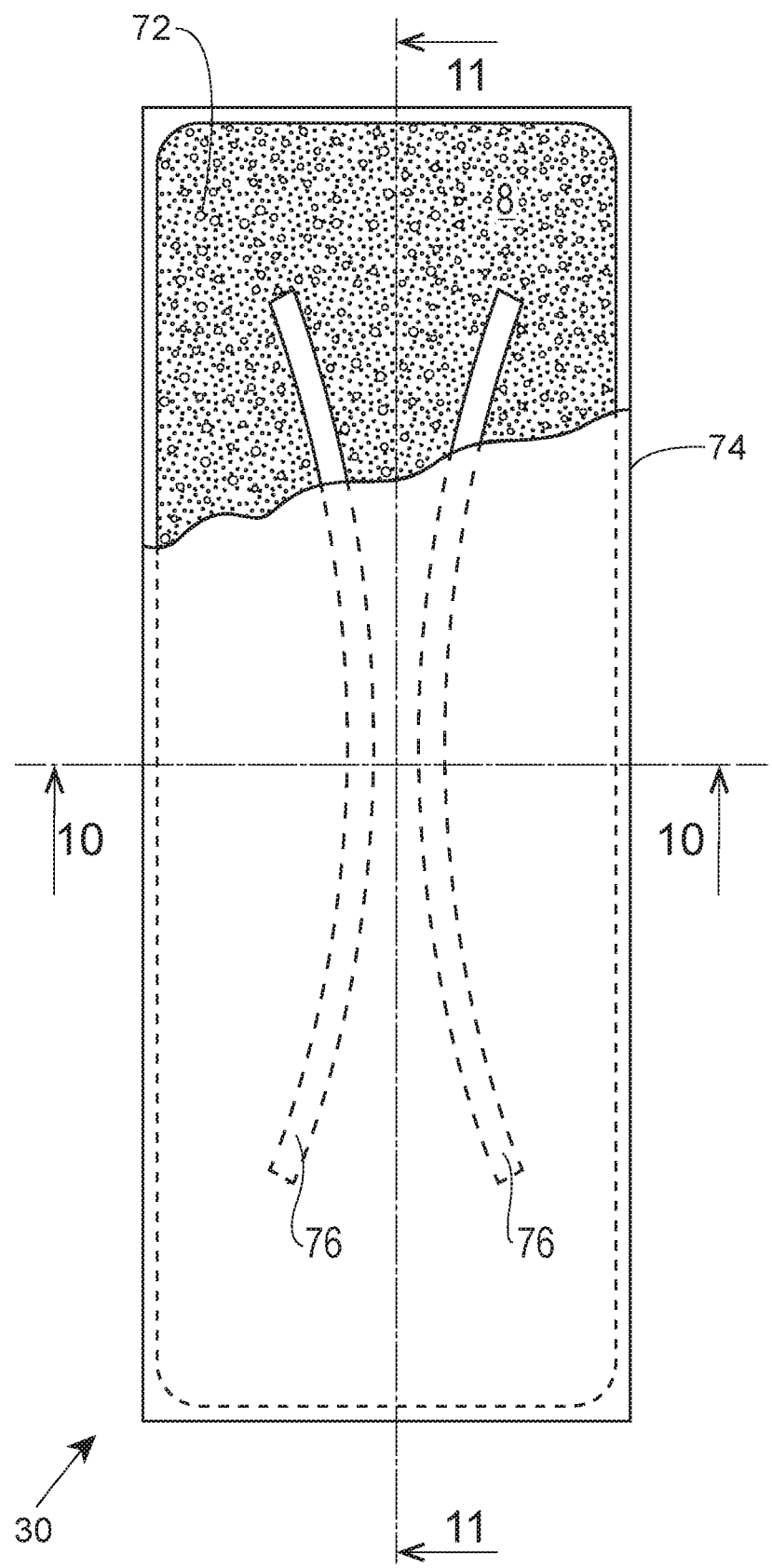
FIG. 9 is a plan view of an example absorbent core or an absorbent article.
Figure 10:
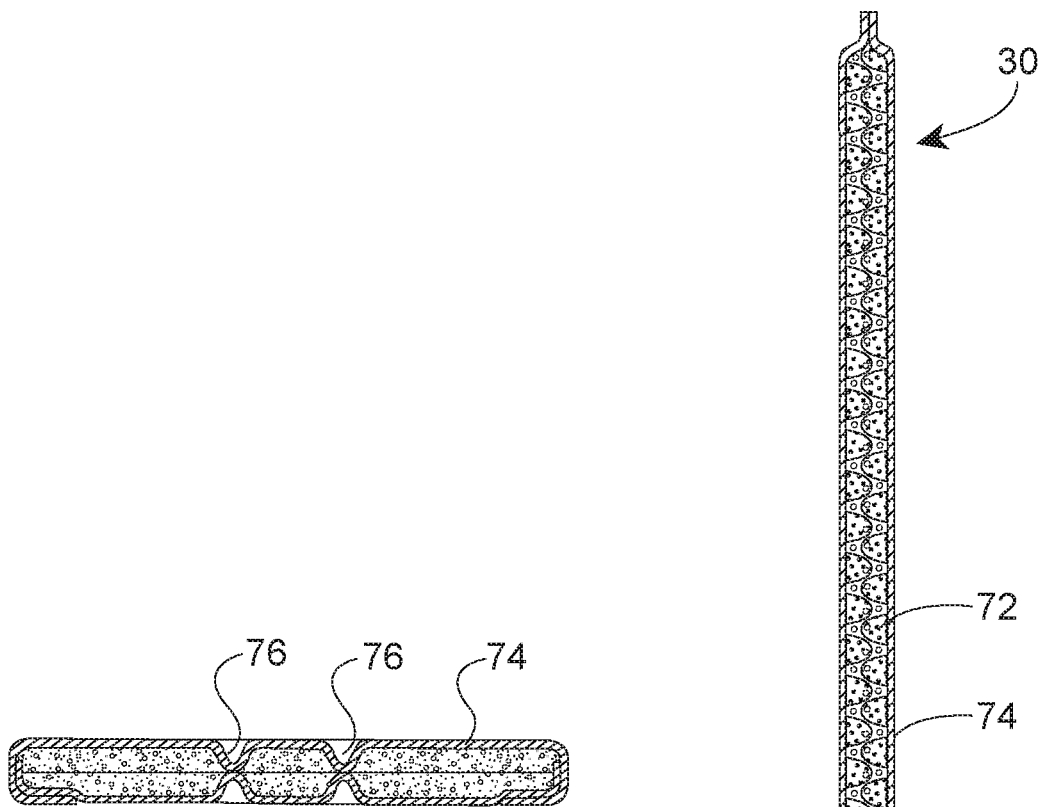
FIG. 10 is a cross-sectional view, taken about line 10-10, of the absorbent core of FIG. 9.
Figure 11:
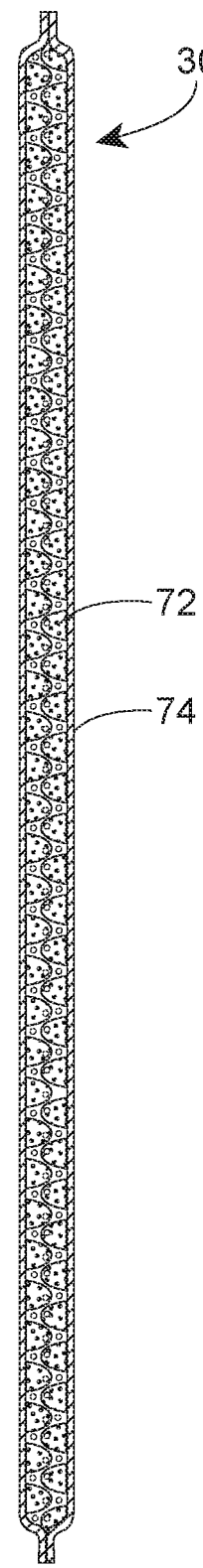
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may be free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material and may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Nonwoven materials of the barrier leg cuffs 32 may comprise mechanical bonds patterns, patterns of apertures, patterns of indicia, and/or patterns of three-dimensional features.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article. Nonwoven materials of the elastic waistbands 46 may comprise mechanical bonds patterns, patterns of apertures, patterns of indicia, and/or patterns of three-dimensional features.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa. The landing zone 44 may comprise mechanical bonds patterns, patterns of apertures, patterns of indicia, and/or patterns of three-dimensional features.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic member formed of an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2. Nonwoven materials of the ears having the fasteners may comprise mechanical bond patterns, patterns of apertures, pattern of indicia, and/or pattern of three-dimensional features and may also comprise ultrasonic bonds.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Sanitary Napkin

Figure 12:
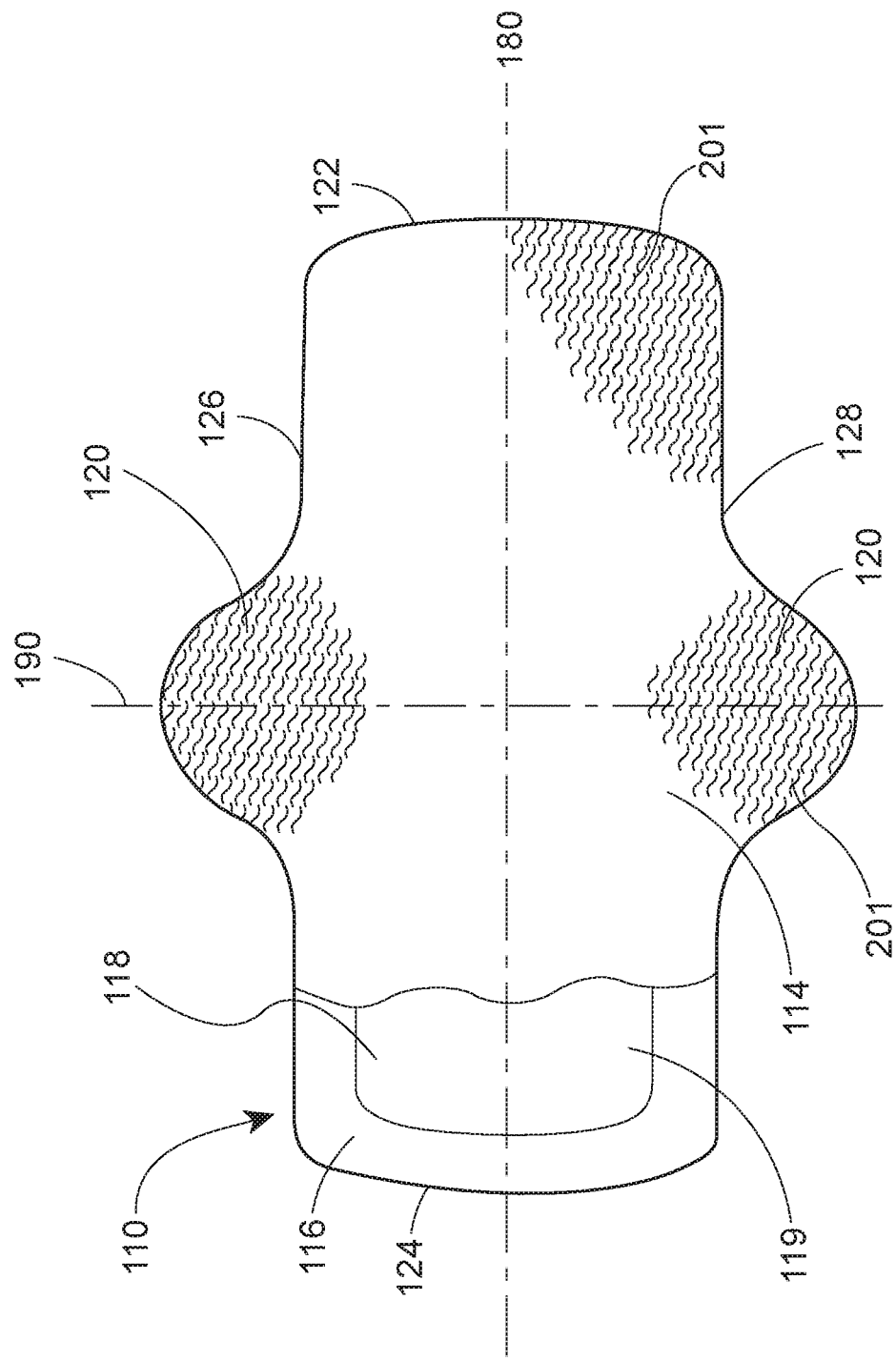
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art. The wings 120 and/or the topsheet 114 may have mechanical bond patterns 201, patterns of indicia, patterns of apertures, and/or patterns of three-dimensional features. The mechanical bond patterns, patterns of indicia, patterns of apertures, and/or patterns of three-dimensional features may be substantially the same, or the same in the wings 120 and the topsheet 114. The mechanical bond patterns, patterns of indicia, patterns of apertures, and/or patterns of three-dimensional features may cover portions of the wings 120 or all of the wings 120 and portions of the topsheet 114 or all of the topsheet 114.

Absorbent Articles With Components for a Uniform Appearance

As referenced above, it may be desirable to have two or more nonwoven material components of absorbent articles that have substantially the same, or the same mechanical bond patterns, patterns of three-dimensional features, patterns of apertures, and/or patterns of indicia (e.g., printing). The two or more nonwoven material components may be substantially the same, the same, or different nonwoven materials. The components may be two or more of an outer cover nonwoven material, a topsheet, a first nonwoven material of a discrete ear laminate, a second nonwoven material of a discrete ear laminate, a nonwoven material of a cuff, a landing zone, and one or more nonwoven materials of a belt, for example, in diaper, pant, or adult incontinence article context. The two components, in a sanitary napkin context, may be a central portion of a topsheet and wings, for example.

Referring again to FIGS. 1-3, the taped absorbent article 10 may comprise a chassis 52 comprising a topsheet 26, a backsheet 28, and an absorbent core 30 positioned at least partially intermediate the topsheet 26 and the backsheet 28. The chassis 52 may also comprise barrier leg cuffs 32. The chassis 52 of the absorbent article 10 may comprise an outer cover nonwoven material 40 joined to the backsheet 28 and in a facing relationship with the backsheet 28. The outer cover nonwoven material 40 may comprise a first mechanical bond pattern 200, a first pattern of indicia, a first pattern of apertures, and/or a first pattern of three-dimensional features. The absorbent article 10 may comprise a discrete ear laminate 42 joined (e.g., bonded) to the chassis 52 in the back waist region 16 or the front waist region 12. The discrete ear laminate 42 may comprise a first nonwoven material 202 on a garment-facing surface of the discrete ear laminate 42 and a second nonwoven material 204 on a wearer-facing surface of the discrete ear laminate 42. The discrete ear laminate 42 may comprise an elastic member 206 positioned at least partially intermediate the first and second nonwoven materials 202, 204. The garment-facing surface of the first nonwoven material 202 may comprise a second mechanical bond pattern 208, a second pattern of indicia, a second pattern of apertures, and/or a second pattern of three-dimensional features. The first and second mechanical bonds patterns 200, 208 may be the same or substantially the same. Likewise, if provided, the first and second patterns of indicia, the first and second patterns of apertures, and/or the first and second patterns of three-dimensional features may be the same, or substantially the same. The wearer-facing surface of the second nonwoven material 204 may comprise a third mechanical bond pattern 210, a third pattern of indicia, a third pattern of apertures, and/or a third pattern of three-dimensional features. The first, second, and third mechanical bonds patterns 202, 208, 210 may be the same or substantially the same. Likewise, if provided, the first, second, and third patterns of indicia, the first, second, and third patterns of apertures, and the first, second, and/or third patterns of three-dimensional features may be the same, or substantially the same.

The various mechanical bond patterns, patterns of indicia, patterns of apertures, and/or patterns of three-dimensional features may cover all of the absorbent article components in which they are on or only portions thereof. For example, a mechanical bond pattern may only be positioned on a portion of an outer cover nonwoven material. The various mechanical bond patterns, patterns of indicia, patterns of apertures, and/or pattern of three-dimensional features may have the same, or substantially the same orientations, on various absorbent article components. For example, a first mechanical bond pattern on an outer cover nonwoven material may have substantially the same orientation on the absorbent article as a second mechanical bond pattern on a garment-facing surface of a discrete ear laminate. This provides for a garment-like appearance and uniformity in the absorbent article.

By providing the same or substantially the same mechanical bond patterns on at least two different components (e.g., an outer cover nonwoven material and a nonwoven material of a discrete ear laminate or discrete side panel of a pant), the absorbent articles of the present disclosure may have a uniform, garment-like appearance leading to the consumer perception of high quality. Similar advantages may be realized using the same or substantially similar patterns of indicia, patterns of three-dimensional features, and/or patterns of apertures on two different absorbent article components comprising nonwoven materials.

The two components on which the mechanical bond patterns, patterns of apertures, patterns of indicia, and/or patterns of three-dimensional features may be non-elastic, allowing the determination as to whether the patterns are the same or substantially the same to be made visually. In an instance where the mechanical bond patterns, patterns of apertures, patterns of indicia, and/or patterns of three-dimensional features are on at least one elastic laminate (e.g., a discrete ear laminate or side panel of a pant), to determine whether the patterns are the same or substantially the same, an absorbent article may be fastened to a surface at the point in which an elastic laminate is attached to the rest of the absorbent article. The elastic laminate may then be pulled away from the remaining portion of absorbent article into a planar configuration such that all elastic contraction is removed, but without tearing the elastic laminate or the chassis to which the elastic laminate is attached. The pattern on the elastic laminate may then be evaluated visually relative to another component of the absorbent article to determine if the patterns are the same or substantially the same.

In addition to the first, second, and/or third nonwoven materials having the same or substantially the same mechanical bond patterns (or patterns of indicia, patterns of three-dimensional features, or patterns of apertures) on three or more different absorbent article components comprising nonwoven materials, the first, second, and/or third nonwoven materials may be substantially the same or the same in composition, basis weight, density, fiber laydown, fiber orientation, nonwoven mechanical bond pattern, method of nonwoven bonding (e.g., air-through, vs. thermal welding), aperturing, and/or fiber type, for example.

Referring to FIGS. 2 and 3, the first mechanical bond pattern 200 may comprise a first plurality of mechanical bond elements 212. The second mechanical bond pattern 208 may comprise a second plurality of mechanical bond elements 214. The third mechanical bond pattern 210 may comprise a third plurality of mechanical bond elements 216. At least some of, or each of, the first plurality of mechanical bond elements 212 may have substantially the same size and/or shape as at least some of, or each of, the second plurality of mechanical bond elements 214. At least some of, or each of, the second plurality of mechanical bond elements 214 may have substantially the same size and/or shape as at least some of, or each of, the third plurality of mechanical bond elements 216. The mechanical bond elements within a mechanical bond pattern may all be the same or substantially the same (i.e., allowing for process tolerances and/or ultrasonic bonds). If patterns of indicia, patterns of apertures, and/or patterns of three-dimensional features are provided, the same concept may apply. At least some of, or all of, the mechanical bond elements may comprise one or more arcuate portions 218. Having mechanical bond elements with arcuate portions may lead to increased softness in nonwoven materials, and may aid in process losses, such as neckdown and strength to resist fuzzing or tearing.

Referring to FIG. 2, the topsheet 26 may comprise a third nonwoven material 205 comprising a fourth mechanical bond pattern 211, patterns of indicia, patterns of apertures, and/or patterns of three-dimensional features. The fourth mechanical bond pattern 211 may comprise a fourth plurality of mechanical bond elements 217. The patterns of indicia, patterns of apertures, and/or patterns of three-dimensional features may comprise individual indicia elements, individual apertures, and/or individual three-dimensional features. In a topsheet context, the mechanical bond pattern 211, patterns of indicia, patterns of apertures, and/or patterns of three-dimensional elements may cover all of the topsheet or portions of the topsheet. The first, second, and third mechanical bonds patterns 202, 208, 210 may be the same or substantially the same as the fourth mechanical bond pattern 211. Likewise, if provided, the first, second, and third patterns of indicia, the first, second, and third patterns of apertures, and the first, second, and/or third patterns of three-dimensional features may be the same as, or substantially the same as, the fourth patterns of indicia, the fourth patterns of apertures, and/or the fourth patterns of three-dimensional elements.

In FIGS. 2 and 3, the mechanical bond patterns are illustrated on the discrete ear laminates 42 with elastic contraction removed so that the mechanical bond patterns may be clearly illustrated.

The mechanical bond patterns, the patterns of indicia, the patterns of apertures, and/or the patterns of three-dimensional features may have any suitable size, shape, and/or spacing. The bond elements of the mechanical bonds patterns may be square, rectangular, arcuate, round, ovate, triangular, linear, non-linear, continuous, discontinuous, or may have any other suitable shapes or configurations. The same principle applies to indicia elements of the patterns of indicia, apertures of the patterns of apertures, and/or three-dimensional features of the patterns of three-dimensional features.

Figure 13:
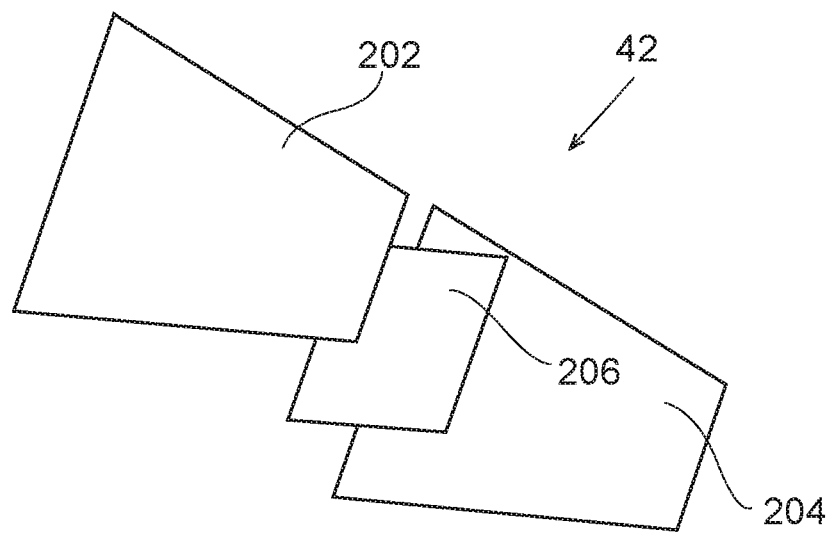
FIG. 13 is a perspective exploded view of a discrete ear laminate of the present disclosure.

FIG. 13 shows an exploded view of a discrete ear laminate 42 of the present disclosure comprising the first nonwoven material 202, the second nonwoven material 204, and the elastic member 206 positioned at least partially therebetween. The elastic member 206 of each of the discrete ear laminates may comprise an elastic film or elastic strands. The elastic film may be apertured or silted for breathability of the discrete ear laminates. In most instances, either the elastic film or the elastic strands will be used in the discrete ear laminates, not both.

Figure 14:
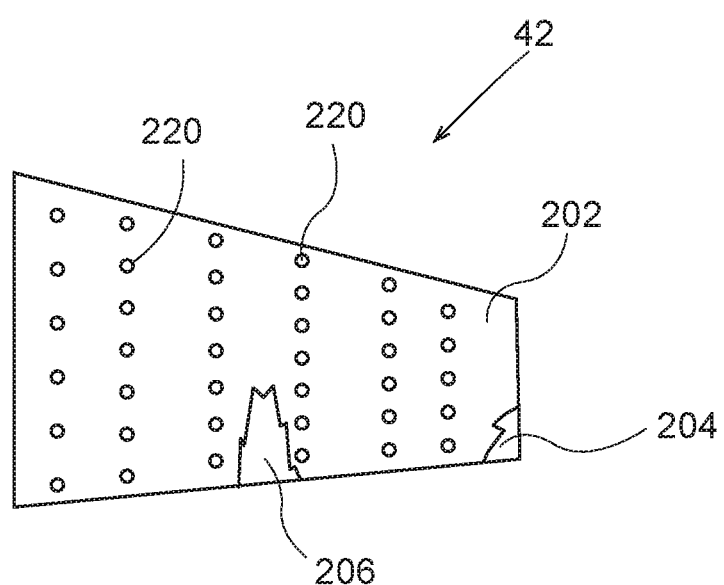
FIG. 14 is a plan view of the discrete ear laminate of FIG. 13 that may comprise a plurality of ultrasonic bonds in addition to any mechanical bonds.

FIG. 14 is a plan view of the discrete ear laminate 42 of FIG. 13 that may comprise a plurality of ultrasonic bonds 220 in addition to any mechanical bond patterns (not shown in FIG. 14 for clarity) on the first and second nonwoven materials 202, 204. The ultrasonic bonds 200 may extend through the first nonwoven material 202, the second nonwoven material 204, and the elastic member 206 at least partially positioned intermediate the first and second nonwoven materials. The ultrasonic bonds 220 may be used in place of adhesives to hold the first nonwoven material 202, the second nonwoven material 204, and the elastic member 206 together. Ultrasonic bonds may be advantageous in that they may be lower in cost and complexity than mechanical bonds due to less raw material streams, and they provide the ability to customize aesthetics and absorbent article performance with different patterns of the ultrasonic bonds. Ultrasonic bonds may also be advantageous in that there is less burn through risk than heated or mechanical bonds.

Figure 15:
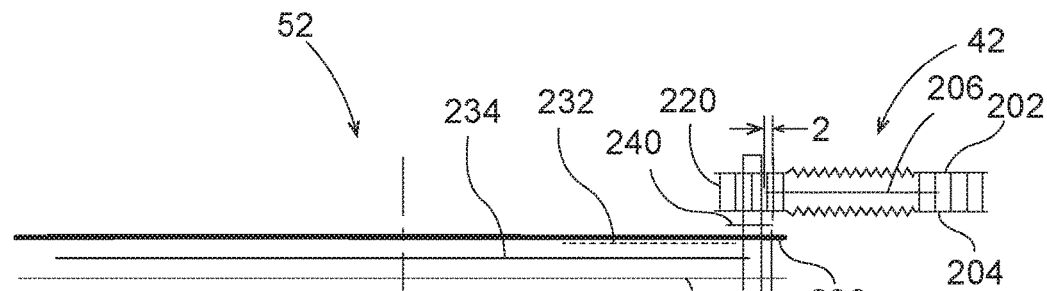
FIGS. 15-18 are a cross-sectional views taken about a longitudinal midpoint of a discrete ear laminate in a direction parallel to a central lateral axis of an absorbent article, illustrating an overlap of various components.

The ultrasonic bonds 220 are also illustrated in part in FIG. 15, although they may extend throughout the discrete ear laminate 42. In the non-elasticized areas of the discrete ear laminate 42, the ultrasonic bonds 220 may be spaced about 0.5 mm to about 20 mm, about 1 mm to about 10 mm, about 1.5 mm to about 4 mm apart, about 2 mm to about 3 mm apart, or about 2.5 mm apart, for example. In the elasticized areas of the discrete ear laminate 42, the ultrasonic bonds may be spaced closer than the non-elasticized areas in view of the elastic member's contraction of that portion of the discrete ear laminate. As the discrete ear laminates 42 are joined to a portion of a chassis 52, at least one and likely a plurality of ultrasonic bonds 200 are within the joinder, as will be discussed in greater detail below. By having at least one and sometimes a plurality of the ultrasonic bonds 200 within the joinder, the discrete ear laminate is better attached and anchored to the portion of the chassis 52.

It is to be appreciated that the ultrasonic bonds 220 may be formed in various ways in accordance with various methods and apparatuses. For example, the ultrasonic bonds 220 may be formed using an ultrasonic horn according to the methods and apparatuses described in U.S. Patent Application Publication Nos. 2018/0042787 and 2018/0042779, filed on Aug. 11, 2017, and published on Feb. 15, 2018. In addition, it is to be appreciated that various systems may be utilized to inspect the quality of the discrete ear laminate 42 and/or individual components thereof during assembly. In some configurations, such quality inspection systems may utilize machine vision systems adapted to detect various types of defects. For example, a supplied elastic film may include defects in the form of through holes and/or relatively weak regions defined by localized high or low basis weights. In turn, such film defects may result in tears during various assembly operations such as activation, ring rolling, and/or stretching in cross and/or machine directions. Such tears may also be exacerbated during bonding operations and/or during use of the assembled product. Thus, quality inspection systems may be configured to inspect films to detect such tears.

Some quality inspection systems may be configured to inspect films at various stages of the laminate assembly process, for example from initial film unwinding to during and/or after bonding with substrates. The inspection system may be configured to inspect the film before, during, and/or after being stretched during assembly operations. For example, in some assembly operations, the film may be stretched in a first occurrence, such as during activation; allowed to partially or fully relax; and then may be stretched in a second occurrence, such as in the cross direction or machine direction before being combined with outer layer substrates. In turn, the film may be inspected before, during, and/or after first and/or second occurrences of stretching. In some configurations, the first occurrence of stretching may create holes in the film in weak regions of the film, and the second occurrence of stretching may make such holes larger, which in turn, make the holes relatively easier to detect. Thus, in some configurations, the film may be inspected during the second occurrence of stretching. In some configurations, the film may be extended less in the first occurrence of stretching than in the second occurrence of stretching. In some configurations, the film may be inspected during a third occurrence of stretching after being bonded to additional substrate layers.

It is to be appreciated that the inspection systems may be configured in various ways, such as disclosed for example in U.S. Pat. No. 8,145,338. In turn, quality inspection systems may include one or more cameras and illumination sources configured in various ways. For example, a camera may be configured to view a first side of the film and illumination sources may configured to illuminate the first side ("front lit") or illuminate an opposing second side of the film ("back lit"). The illumination source may also be directed at a desired angle with respect to the film so as to reduce specular reflections observed by the camera. If a defect is detected in the film, a signal may then be delivered to reject and/or alarm systems. In addition to defects, it is also to be appreciated that the inspection system may be configured to detect various parameters. For example, the inspection system may be configured to detect the edges of the film, which in turn, may allow for the detection of loss of control of the film at lamination. In another example, the inspection system may be configured to detect the presence or absence of substrate layers after folding and/or bonding with the film.
Joinder of Discrete Ear Laminates to Absorbent Article Chassis One concern with discrete ear laminates or discrete side panels of a pant is their joinder to the chassis. The joinder needs to be strong enough to support significant stretching of the discrete ear laminates during donning of a taped absorbent article and during wear. Discrete ear laminate tearing and/or chassis tearing during donning and/or wear would be viewed as a total failure of the absorbent article. What the inventors have found is that certain elements need to be overlapped at a point of joinder between the chassis and the discrete ear laminate to achieve optimal performance and significantly reduce discrete ear laminate tearing and/or chassis tearing. Essentially, the joinder needs to be stronger than the materials in the discrete ear laminate and the materials in the chassis that receive forces from discrete ear laminate stretching. As an example, the joinder between a portion of the discrete ear laminate and the back or front waist region of a chassis may comprise an overlap of: an adhesive bond, a mechanical bond, one or more ultrasonic bonds formed in the discrete ear laminate 42, a portion of the first nonwoven material 202 of the discrete ear laminate 42, and a portion of the second nonwoven material 204 of the discrete ear laminate 42. The overlap may comprise a portion of the elastic member 206 for added strength in the joinder. The overlap may not comprise a mechanical bond that overlaps with the adhesive bond and the elastic member 206. The overlap may have a width, taken in a direction parallel to a central lateral axis of the absorbent article 10, in the range of about 10 mm to about 50 mm or about 15 mm to about 35 mm, specifically reciting all 0.1 mm increments within the specified ranges and all ranges formed therein or thereby.

A taped absorbent article may comprise a chassis comprising a topsheet, a backsheet, an absorbent core positioned at least partially intermediate the topsheet and the backsheet, a front waist region, and a back waist region. The absorbent article may comprise a discrete ear laminate comprising a first nonwoven material, a second nonwoven material, and an elastic member positioned at least partially intermediate the first nonwoven material and the second nonwoven material. The discrete ear laminate may comprise a plurality of ultrasonic bonds. A joinder between a portion of the discrete ear laminate and the back or front waist region of the chassis may comprise an overlap of: an adhesive bond, a mechanical bond, one or more of the ultrasonic bonds of the discrete ear laminate, a portion of the first nonwoven material of the discrete ear laminate, and a portion of the second nonwoven material of the discrete ear laminate. The overlap may comprise a portion of the elastic member for added strength. The overlap may have a width in the range of about 15 mm to about 35 mm, taken in a direction parallel to a central lateral axis of the absorbent article, and other ranges stated herein

EXAMPLES

Referring to FIGS. 15-18, various examples of overlaps between portions of the chassis 52 and the discrete ear laminates 42 are illustrated. In all of FIGS. 15-18, the following reference numbers indicate the following components, although only FIG. 15 has been labeled since the components are the same in each of FIGS. 15-18 and only their location is varied in some figures:

202—First nonwoven layer of discrete ear laminate 42
204—Second nonwoven layer of discrete ear laminate 42
206—Elastic member of discrete ear laminate 42
220—Ultrasonic bonds
230—Outer cover nonwoven material
232—Backsheet lamination glue
234—Backsheet film
236—Cuff nonwoven
238—Mechanical bond
240—Adhesive bond In the example cross-sectional illustrations of FIGS. 15-18 and the data in Chart 1, various dimensions were evaluated to determine the best ways to anchor a discrete ear laminate to a front or a back waist region of the chassis to provide the joinder with the most strength during stretching, donning, and/or wear. In all of the examples, a discrete back ear laminate was attached to a portion of a back waist region of the chassis on a garment-facing side of the chassis, but it will be understood that a discrete front ear laminate may be attached to a portion of a front waist region of the chassis in a similar or the same fashion. The discrete ear laminates may also be joined to a wearer-facing side of the chassis in the front or back waist regions. The cross-sectional illustrations are taken about a longitudinal midpoint of the discrete ear laminate in a direction parallel to a central lateral axis of the absorbent article. Only one discrete ear laminate is illustrated in the examples, but most configurations will have discrete ear laminates on each of the ends and have the same overlaps at the joinder.

CHART 1

Figure 16:
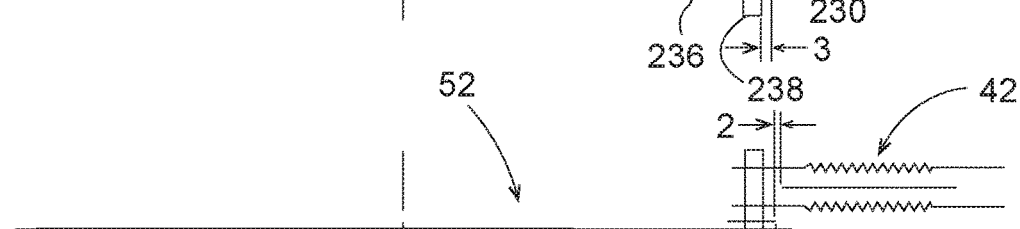

| Examples | Description | Elastic member Overlap With Adhesive Bond | Back Ear Adhesive Bond Outboard of mechanical bond | Back Ear Adhesive bond Basis Weight | Peak Tensile Strength Mean | Lower 95$^{th}$ Percentile |
|---|---|---|---|---|---|---|
| FIG. 15 | Control | 2 mm | 3 mm | 13.3 gsm | 44N | 36N |
| FIG. 16 | Negative Control | −2 mm | 3 mm | 13.3 gsm | 42N | 30N |
| FIG. | Moved | 5 mm | 3 mm | 13.3 gsm | 49N | 41N |

CHART 1-continued

Figure 18:
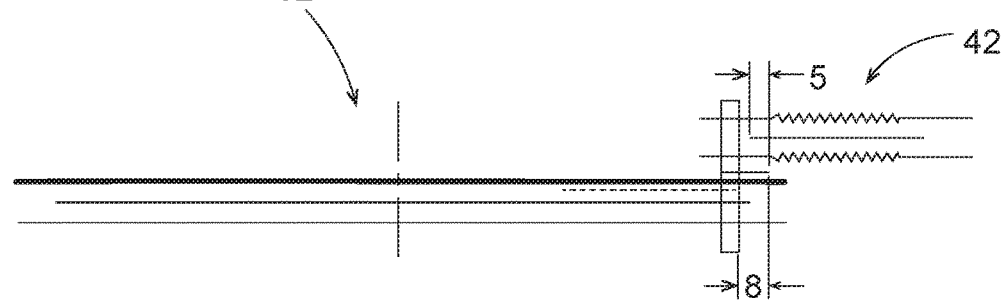

| Examples | Description | Elastic member Overlap With Adhesive Bond | Back Ear Adhesive Bond Outboard of mechanical bond | Back Ear Adhesive bond Basis Weight | Peak Tensile Strength Mean | Lower 95th Percentile |
|---|---|---|---|---|---|---|
| 17 | Discrete Ear Laminate Inboard (relative to Control) | | | | | |
| FIG. 18 | Moved Discrete Ear Laminate Inboard, Moved Mechanical Bond Inboard (both relative to Control) | 5 mm | 8 mm | 13.3 gsm | 47N | 41N |
| FIG. 18' | Moved Discrete Ear Laminate Inboard, Moved Mechanical Bond Inboard, Increase basis weight of adhesive bond (all relative to Control) | 5 mm | 8 mm | 16.6 gsm | 47N | 43N |

The example of FIG. 15 shows a discrete back ear laminate that has an elastic member 206 overlap with the adhesive bond 240 of 2 mm, the adhesive bond 240 is outboard of the mechanical bond 238 by 3 mm, and the adhesive of the adhesive bond 240 has a basis weight of 13.3 gsm. One or more ultrasonic bonds 220 formed in the discrete ear laminate are overlapped by the mechanical bond 238 and the adhesive bond 240 to better anchor the discrete ear laminate 42 to the chassis 52. The example of FIG. 15 is considered the "control."

The example of FIG. 16 shows a discrete back ear laminate that has an elastic member 206 overlap with the adhesive bond 240 of −2 mm (meaning no overlap), the adhesive bond 240 is outboard of the mechanical bond 238 by 3 mm, and the adhesive of the adhesive bond 240 has a basis weight of 13.3 gsm. One or more ultrasonic bonds 220 formed in the discrete ear laminate are overlapped by the mechanical bond 238 and the adhesive bond 240. The example of FIG. 16 is considered the "negative control."

Figure 17:
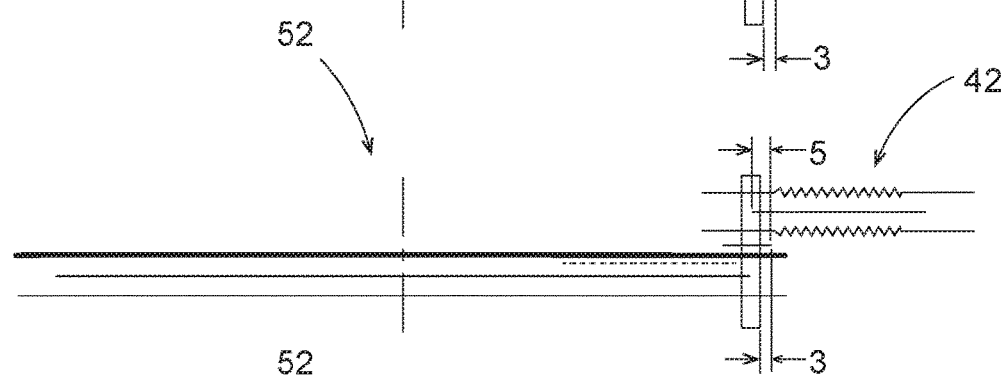

The example of FIG. 17 shows a discrete back ear laminate that has an elastic member 206 overlap with the adhesive bond 240 of 5 mm, the adhesive bond 240 outboard of the mechanical bond 238 by 3 mm, and the adhesive of the adhesive bond 240 has a basis weight of 13.3 gsm. The example of FIG. 17 is considered an improved example of the present disclosure. One or more ultrasonic bonds 220 formed in the discrete ear laminate are overlapped by the mechanical bond 238 and the adhesive bond 240 to better anchor the discrete ear laminate 42 to the chassis 52. In the example of FIG. 17 the entire discrete ear laminate was moved laterally inboard on the chassis relative to the control of FIG. 15.)

The example of FIG. 18 shows a discrete back ear laminate that has an elastic member 206 overlap with the adhesive bond 240 of 5 mm, the adhesive bond 240 outboard of the mechanical bond 238 by 8 mm, and the adhesive of the adhesive bond 240 has a basis weight of 13.3 gsm. The example of FIG. 18 is considered an improved example of the present disclosure. One or more ultrasonic bonds 220 formed in the discrete ear laminate are overlapped by the mechanical bond 238 and the adhesive bond 240 to better anchor the discrete ear laminate 42 to the chassis 52. In the example of FIG. 18 the entire discrete ear laminate was moved laterally inboard on the chassis relative to the control of FIG. 15 and the mechanical bond 238 was move laterally inboard on the chassis relative to the control of FIG. 15. The example of FIG. 18' merely has a different basis weight of the adhesive of the adhesive bond 240 of 16.6 gsm and is otherwise the same as the example of FIG. 18. The examples of FIG. 18 and FIG. 18' are considered an improved example of the present disclosure.

Figure 19:
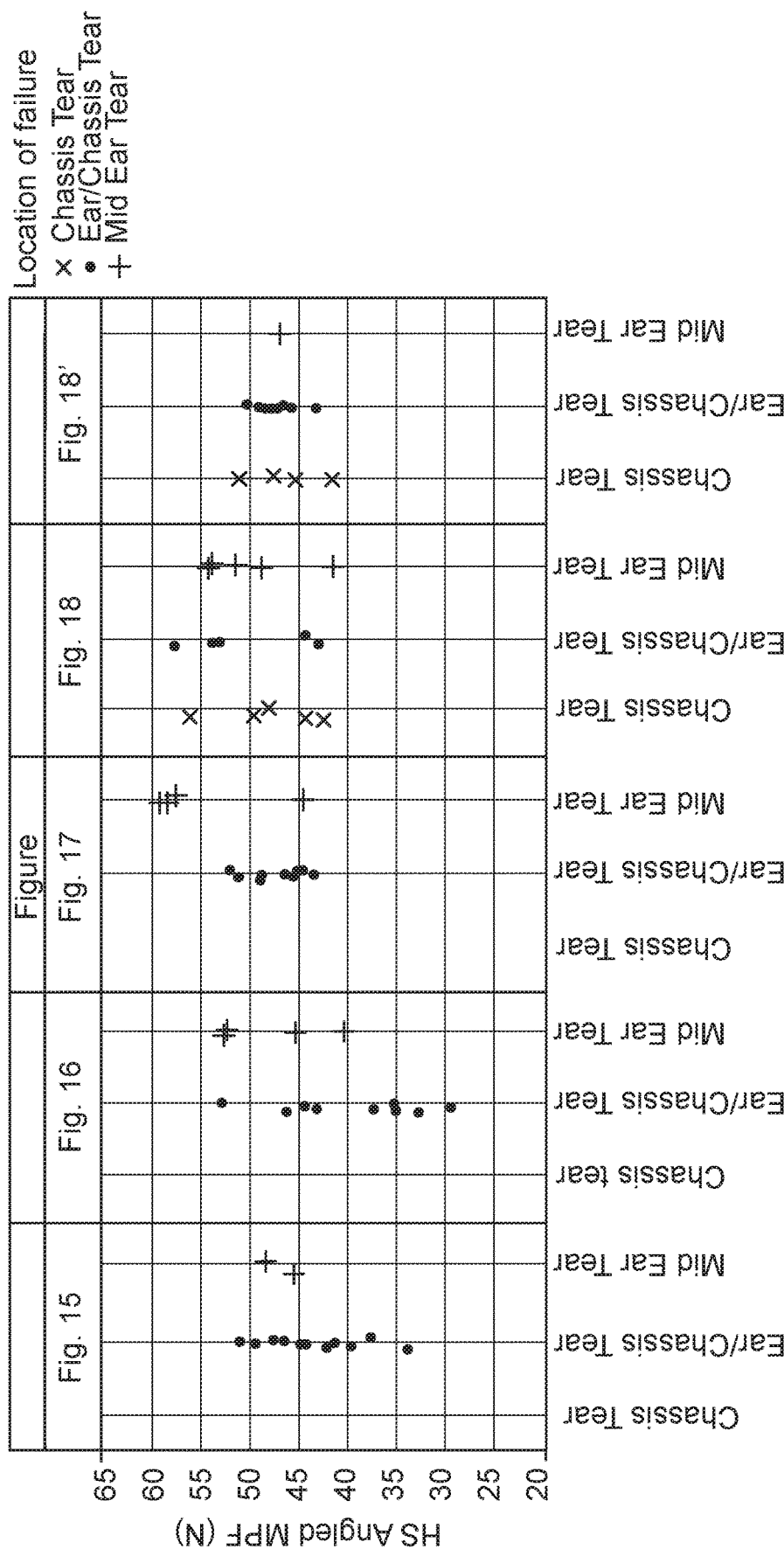
FIG. 19 is a graph illustrating ultimate tensile strength and failure modes of the discrete ear laminates and/or the chassis of FIGS. 15-18, when the discrete ear laminates are subjected to an outwardly (i.e., away from the chassis) pulling force.

As can be seen from the data in Chart 1, with the movement of the discrete ear laminate laterally inboard relative to the chassis (FIG. 17), the mean force increased by 5 N. With the movement of the discrete ear laminate laterally inboard relative to the chassis and movement of the mechanical bond laterally inboard relative to the chassis (FIG. 18), the mean force increased by 3 N. With the movement of the discrete ear laminate laterally inboard relative to the chassis, movement of the mechanical bond laterally inboard relative to the chassis, and the 3 gsm increase in basis weight of the adhesive of the adhesive bond, the means force increased by 3 N. The results are illustrated graphically in FIG. 19. As can be seen, the number of failures at a lower force (under 40 N) significantly decreased to zero for the examples of FIGS. 17, 18, and 18'. Failures are defined as tearing of the chassis, tearing of the discrete ear laminate, or tearing of both the chassis and the discrete ear laminate.

Another factor that appeared to decrease the failures is the overlap of the elastic member 206 with the adhesive bond and/or the mechanical bond and generally more overlap of an inboard portion of the discrete ear laminate with the chassis.

Breathability of Discrete Ear Laminates

The discrete ear laminates of the present disclosure may have a high breathability to promote good skin health and reduced sweating for a wearer of an absorbent article. The discrete ear laminates may have a water vapor transmission rate in the range of about 500 MVTR (g/m$^2$/24 hrs) to about 2,500 MVTR (g/m$^2$/24 hrs), about 500 MVTR (g/m$^2$/24 hrs) to about 2,000 MVTR (g/m$^2$/24 hrs), about 750 MVTR (g/m$^2$/24 hrs) to about 1500 MVTR (g/m$^2$/24 hrs), or about 1,000 MVTR (g/m$^2$/24 hrs) to about 1300 MVTR (g/m$^2$/24 hrs), specifically reciting all 0.5 MVTR (g/m$^2$/24 hrs) increments within the specified ranges and all ranges formed therein or thereby. All MVTR (g/m$^2$/24 hrs) ranges are according to the Water Vapor Transmission Rate Test herein.

Chart 2 below compares an example of the present disclosure to two related art ear laminates. All of the discrete ear laminates have a first nonwoven material, a second nonwoven material, and an elastic film positioned therebetween. As can been seen below, the discrete ear laminates of the present disclosure have a much higher water vapor transmission rate, and thereby breathability, than the related art ear laminates

CHART 2

| Samples | MVTR (g/m²/24 hrs) |
| --- | --- |
| Present Disclosure back ear laminate with ultrasonic bonds and elastic film | 1119 |
| Pampers Swaddlers back ear laminate with elastic film | 272 |
| Huggies Little Snugglers back ear laminate with elastic film | 344 |

Water Vapor Transmission Rate Test

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2 C.° and 50%±2% relative humidity. Articles are preconditioned at 23° C.±2C.° and 50%±2% relative humidity for two hours prior to testing.

Obtain a test specimen of back ear laminate material by removing it from an absorbent article, if necessary. When excising the test specimen from an absorbent article, use care to not impart any contamination or distortion to the test specimen during the process, and note the wearer-facing side. The test specimen is obtained from an area free of folds, wrinkles, bond sites, tape tabs or any other material that is not inherently meant to be part of the back ear laminate itself. A test specimen from both sides (right and left) of the absorbent article is obtained, and test specimens from five substantially similar articles are prepared for testing (e.g., 5 right and 5 left).

Glass straight walled, cylindrical vials, 95 mm tall with a 17.8 mm internal diameter at the opening are used as WVTR test vials. These vials provide a Surface Area of 2.487*10' m². Each test vial is filled with deionized water accurately to a level 25.0 mm±0.1 mm from the upper lip of the vial's opening. The test specimen is placed over the vial's opening such that the wearer-facing side faces the inside of the vial and the material remains in a relaxed (non-stretched) state. The test specimen is then secured around the vial's circumference with an elastic band. The test specimen is further sealed by wrapping Teflon tape around the vial's circumference. The Teflon tape is applied up to the top edge of the vial but should not cover any portion of the vial's opening.

The wrapping of Teflon tape extends down the vial's circumference so that it covers any exposed edges of the test specimen thereby preventing any edge leaks. A preferred Teflon tape is a thread sealant tape 0.25" wide available from McMaster Car (cat. No. 459111), or equivalent. The mass of the entire vial assembly (vial+water+specimen+elastic band+Teflon tape) is weighed to the nearest 0.0001 gram and recorded as Initial Mass. Repeat in like fashion until vial assemblies for all 10 test specimens are prepared.

The vial assemblies are placed upright in a mechanical convection oven (e.g., Lindberg/BlueM oven available from Thermo Scientific, or equivalent) maintained at 38°±10° C. for 24 hours, taking care to avoid contact between the water in the vials and the test specimens. After 24 hours has elapsed, the vial assemblies are removed from the oven and allowed to cool to room temperature. The mass of each vial assembly is measured to the nearest 0.0001 gram and recorded as Final Mass. The WVTR is calculated using the following equation:

$$WVTR\ (g/m^2/24\ hrs) = [\text{Initial Mass (g)} - \text{Final Mass (g)}]/\text{Surface Area (m}^2)$$

Calculate the arithmetic mean for WVTR for all 5 substantially similar absorbent articles (ten test specimens; 5 right and 5 left) and report to the nearest 1 g/m²/24 hrs.

Examples/Combinations:

A. A taped absorbent article comprising:
   a chassis comprising:
      a topsheet;
      a backsheet;
      an absorbent core positioned at least partially intermediate the topsheet and the backsheet; and
      an outer cover nonwoven material joined to the backsheet, wherein the outer cover nonwoven material comprises a first mechanical bond pattern; and
   a discrete ear laminate joined to the chassis, wherein the discrete ear laminate comprises:
      a first nonwoven material comprising a garment-facing surface;
      a second nonwoven material comprising a wearer-facing surface;
      an elastic member positioned at least partially intermediate the first and second nonwoven materials; and
      a plurality of ultrasonic bonds;
      wherein the garment-facing surface of the first nonwoven material comprises a second mechanical bond pattern, and wherein the first and second mechanical bond patterns are substantially the same; and
      wherein the wearer-facing surface of the second nonwoven material comprises a third mechanical bond pattern, and wherein the first and second mechanical bond patterns are substantially the same.

B. The taped absorbent article of Paragraph A, wherein the first mechanical bond pattern comprises a first plurality of mechanical bond elements, wherein the second mechanical bond pattern comprises a second plurality of mechanical bond elements, and wherein the first plurality of mechanical bond elements have the same size and same shape as the second plurality of mechanical bond elements.

C. The taped absorbent article of Paragraph B, wherein the first mechanical bond pattern has substantially the same orientation in the taped absorbent article as the second mechanical bond pattern.

D. The taped absorbent article of any one of Paragraphs A-C, wherein the basis weight of the outer cover nonwoven material and the basis weight of the first nonwoven material are substantially the same, and wherein the basis weight of the outer cover nonwoven material and the basis weight of the second nonwoven material are substantially the same.

E. The taped absorbent article of any one of Paragraphs A-D, wherein the composition of the outer cover nonwoven material and the composition of the first nonwoven material are substantially the same, and wherein the composition of the outer cover nonwoven material and the composition of the second nonwoven material are substantially the same.

F. The taped absorbent article of any one of Paragraphs A-E, wherein the elastic member comprises a plurality of elastic strands or an elastic film.

G. The taped absorbent article of any one of Paragraphs A-F, wherein the discrete ear laminate comprises a plurality of ultrasonic bonds; and
   wherein a joinder between a portion of the discrete ear laminate and a back or front waist region of the taped absorbent article comprises:
      an overlap of:
         an adhesive bond;

a mechanical bond;
one of the ultrasonic bonds;
the first nonwoven material; and
the second nonwoven material.

H. The taped absorbent article of Paragraph G, wherein the overlap comprises a portion of the elastic member.

I. A taped absorbent article comprising:
a chassis comprising:
a topsheet;
a backsheet;
an absorbent core positioned at least partially intermediate the topsheet and the backsheet; and
an outer cover nonwoven material joined to the backsheet, wherein the outer cover nonwoven material comprises a first mechanical bond pattern;
an ultrasonically bonded discrete ear laminate joined to the chassis, wherein the discrete ear laminate comprises:
a first nonwoven material having a garment-facing surface;
a second nonwoven material having a wearer-facing surface; and an elastic member positioned at least partially intermediate the first and second nonwoven materials; and
wherein a surface of the first nonwoven material or a surface of the second nonwoven material comprises a second mechanical bond pattern, and wherein the first and second mechanical bond patterns are substantially the same, and wherein the outer cover nonwoven material is substantially the same as the first nonwoven material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. A taped absorbent article comprising:
a chassis comprising:
a topsheet;
a backsheet;
an absorbent core positioned at least partially intermediate the topsheet and the backsheet;
a front waist region;
a back waist region; and
an outer cover nonwoven material;
an ultrasonically bonded discrete ear laminate comprising:
a first nonwoven material;
a second nonwoven material; and
an elastic member positioned at least partially intermediate the first nonwoven material and the second nonwoven material;
the discrete ear laminate comprising a plurality of ultrasonic bonds; and
a joinder between a portion of the discrete ear laminate and the back or front waist region comprising:
an overlap of:
an adhesive bond;
a portion of the elastic member;
one of the ultrasonic bonds; and
a portion of the first nonwoven material; and
a portion of the second nonwoven material;
wherein the first nonwoven material comprises a garment-facing surface comprising a first nonwoven mechanical bond pattern; wherein the first nonwoven mechanical bond pattern extends laterally from adjacent to a first side edge to adjacent to a second side edge of the discrete ear laminate;
wherein the outer cover nonwoven material comprises a second nonwoven mechanical bond pattern, and wherein the first and second nonwoven mechanical bond patterns are substantially the same.

2. The taped absorbent article of claim 1, wherein the overlap comprises a mechanical bond.

3. The taped absorbent article of claim 2, wherein the discrete ear laminate has a water vapor transmission rate in the range of about 1,000 MVTR ($g/m^2/24$ hrs) to about 1,300 MVTR ($g/m^2/24$ hrs), according to the Water Vapor Transmission Rate Test.

4. The taped absorbent article of claim 1, wherein the elastic member comprises a plurality of elastic strands or an elastic film.

5. The taped absorbent article of claim 1, wherein a basis weight of the outer cover nonwoven material and a basis weight of the first nonwoven material are substantially the same.

6. The taped absorbent article of claim 1, wherein a basis weight of the outer cover nonwoven material and a basis weight of the second nonwoven material are substantially the same.

7. The taped absorbent article of claim 1, wherein the outer cover nonwoven material and the first nonwoven material are substantially the same, and wherein the outer cover nonwoven material and the second nonwoven material are substantially the same.

8. The taped absorbent article of claim 1, wherein the elastic member is an elastic film comprising a plurality of apertures.

9. The taped absorbent article of claim 1, wherein the absorbent article comprises one or more elastic waistbands.

10. The taped absorbent article of claim 9, wherein the one or more elastic waistbands comprise a nonwoven material comprising a pattern selected from the group consisting of a mechanical bond pattern, a pattern of apertures, a pattern of indicia, a pattern of three-dimensional features, and combinations thereof.

* * * * *